United States Patent
O'Lenick, Jr.

(10) Patent No.: US 7,361,721 B1
(45) Date of Patent: Apr. 22, 2008

(54) CROSSLINKED SILICONE POLYMERS

(76) Inventor: Anthony J. O'Lenick, Jr., 2170 Luke Edwards Rd., Dacula, GA (US) 30019

( * ) Notice: Subject to any disclaimer, the term of this patent is extended or adjusted under 35 U.S.C. 154(b) by 285 days.

(21) Appl. No.: 11/257,964

(22) Filed: Oct. 26, 2005

Related U.S. Application Data

(60) Provisional application No. 60/706,343, filed on Aug. 9, 2005.

(51) Int. Cl.
*C08G 77/46* (2006.01)
(52) U.S. Cl. .......................... 528/31; 528/25; 525/479
(58) Field of Classification Search ...................... None
See application file for complete search history.

(56) References Cited

U.S. PATENT DOCUMENTS

| | | | |
|---|---|---|---|
| 4,877,854 A * | 10/1989 | Hattori et al. ................ 528/15 |
| 5,086,148 A * | 2/1992 | Jochum et al. ................ 529/15 |
| 5,112,512 A * | 5/1992 | Nakamura .................. 252/62.2 |
| 5,236,986 A * | 8/1993 | Sakuta ........................ 524/267 |
| 5,412,004 A * | 5/1995 | Tachibana et al. ............ 524/27 |
| 5,889,108 A * | 3/1999 | Zhang ........................ 524/862 |
| 6,139,823 A | 10/2000 | Drechsler et al. |
| 6,200,581 B1 * | 3/2001 | Lin et al. .................... 424/401 |
| 6,239,244 B1 * | 5/2001 | Stepp et al. .................. 528/15 |
| 6,747,115 B2 * | 6/2004 | Sakuta ........................ 528/31 |
| 7,019,098 B2 * | 3/2006 | Hupfield ...................... 528/31 |

* cited by examiner

*Primary Examiner*—Marc S. Zimmer

(57) ABSTRACT

The present invention relates to a series of crosslinked silicone polymers that by virtue of the nature of the crosslinker, have unique solubility and properties. These include improved tolerance for oily materials and water soluble materials. These polymers find use in personal care applications like pigmented products. In the personal care arena, solid products that do not experience syneresis are important. Syneresis is a condition that exists in a solid product that causes a liquid that is incompatible to ooze out, which is cosmetically unacceptable.

28 Claims, No Drawings

CROSSLINKED SILICONE POLYMERS

CLAIM OF BENEFIT TO PROVISIONAL APPLICATION

This patent application claims the benefit of the earlier-field U.S. Provisional Patent Application entitled "Crosslinked Silicone Polymers", having Ser. No. 60/706,343 and filed Aug. 9, 2005

FIELD OF THE INVENTION

The present invention relates to a series of crosslinked silicone polymers that by virtue of the nature of the crosslinker, have unique solubility and properties. These include improved tolerance for oily materials and water soluble materials. These polymers find use in personal care applications like pigmented products. In the personal care arena, solid products that do not experience syneresis are important. Syneresis is a condition that exists in a solid product that causes a liquid that is incompatible to ooze out, which is cosmetically unacceptable.

BACKGROUND OF THE INVENTION

The term silicone resin has been applied both to and misapplied to a variety of materials over time. Silicone resins as used herein refer to a series of products which include at least two silicone backbones that are joined by a "crosslinking group". The number of crosslinking groups that are present as a percentage of the total molecular weight will determine the properties of the resulting polymer.

If there are no crosslinking groups; the polymer can freely rotate and consequently is an oily liquid. If a few crosslinking groups are introduced, the ability to rotate is slightly restricted and the oily material becomes "rubbery". The rubbery material should be referred to as an elastomer. The properties are morel like a rubber band than plastic. As the percentage of crosslinking increases still the molecule becomes rigid. This class of compounds are resins. If you hit the film with a hammer and it shatters it is a resin, if it bounces it is an elastomer and if it squirts out is a silicone fluid.

The difficulty in determining if a product is a fluid an elastomer or resin occurs for products that lie between the classifications. Specifically, when does an elastomer become a resin? While this exact point is of academic interest it does not have nay practical significance to the present invention.

There are a number of classes of resin compounds differing in the nature of the crosslinker. One class is the so called "Q resins".

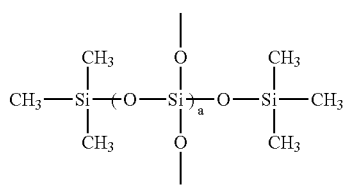

The oxygen that needs another bond connects to another polymer as shown:

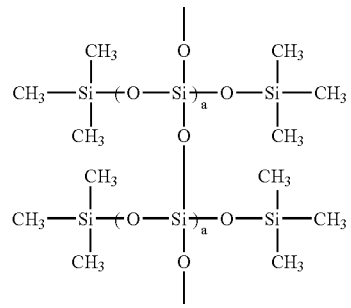

The crosslinking group is —O—. This type of resin is disclosed in U.S. Pat. No. 6,139,823, incorporated herein by reference. This type of material has a group, the so called "Q" group in which a Si has four oxygen atoms attached. In the above case it is the group that is within the "a" subscript. This type of resin is very powdery and is rarely used without a plasticizer. This class of compounds can also dry the skin.

The next class of resin contain alkyl connecting groups.

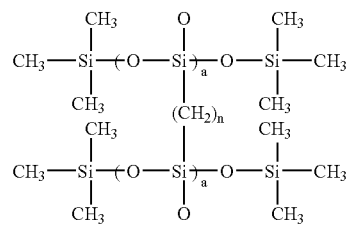

In the case where n=1 acetylene is used as a crosslinking reactant. It is reacted with a silanic hydrogen polymer. As n is increased the reactant is an alpha omega divinyl compound.

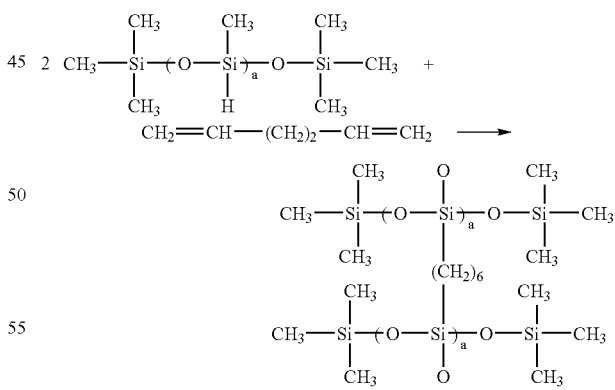

The reaction is called hydrosilylation and provides the linking groups between the molecules. The reaction is generally run in solvent like cyclomethicone (D4 or D5 or hexamethyl disiloxane) or in volatile organic like isododecane. A catalyst generally a platinum one is used to effect the reaction. Chloroplatinic acid or Karnsteadt catalyst are preferred. The resulting material is a viscous liquid that when the solvent evaporates provides a film.

The present invention makes use of novel crosslinking reagents that provide groups that significantly alter the solubility of the resin. This is done by introducing fatty ester linkages, water soluble groups linked with fatty esters and glyceryl esters. Not only does the solubility change, the ability to formulate solid products free from syneresis also occurs. Another unexpected benefit is that the ester moiety provides improved biodegradation of the resin making the resin "more green" and improving consumer acceptability. None of these advantageous are present in the compounds known heretofore.

THE INVENTION

Object of the Invention

It is the object of the present invention to provide a series of silicone polymers that have differing crosslinking groups. The groups are all reactive with silanic hydrogen to provide a crosslinked product. The crosslinkers all have ester groups and either a large fatty group or a water soluble group.

Another object of the present invention is to provide a series of products suitable for formulation into personal care products providing improved skin feel (i.e. not drying like Q resins) and having improved solubility over alkyl linked polymers.

Other objects of the invention will become clear as one reads the specification attached hereto.

All % given herein are % by weight, all temperatures are ° C., all patents and publications referred to herein are incorporated herein by reference in their entirety as appropriate.

SUMMARY OF THE INVENTION

The present invention relates to a series of silicone resins that (a) provide improved water or oil solubility depending upon the specific crosslinker chosen; (b) provide a polar ester linkage in the molecules, which in addition to being more polar than alkylene groups, is also more biodegradable; (c) provide products with a low degree of syneresis when placed in lipstick systems.

The compounds of the present invention are made by reacting specific alpha omega multi-vinyl compounds with silicone compounds that contain multiple silanic hydrogen (Si—H) groups. The reaction is conducted in a suitable solvent selected from the group consisting of cyclomethicone (D-4 and D-5 and mixtures thereof) and isoalkanes (isododecane).

DETAILED DESCRIPTION OF THE INVENTION

Resins of the present invention are a class of silicone compounds which are prepared by the reaction of a polyvinyl compound reacted with a silanic hydrogen containing compound.

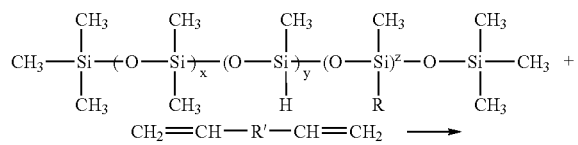

-continued

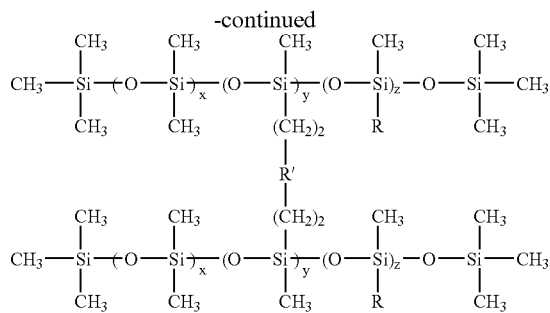

wherein;

x is an integer ranging from 0 to 2000;

y is an integer ranging from 2 to 200;

z is an integer ranging from 0 to 200;

R is selected from the group consisting of H, —(CH$_2$)$_e$—CH$_3$;

—(CH$_2$)$_3$—O—(CH$_2$CH$_2$O)$_f$(CH$_2$CH(CH$_3$)O)$_g$ (CH$_2$CH$_2$O)$_h$—H;

e is an integer ranging from 6 to 35;

f is an integer ranging from 0 to 20;

g is an integer ranging from 0 to 20;

h is an integer ranging from 0 to 20.

The reactions are typically carried out in a solvent, either volatile silicone (cyclomethicone (D4 or D5 or mixtures thereof) or hydrocarbon solvent like isododecane. A suitable hydrosilylation catalyst like chloroplatinic acid or Karnstedt catalyst are used.

The value of "y" determines the degree of crosslinking and consequently if the product is resinous or elastomeric. Elastomeric materials are compounds that are crosslinked to a lesser extent than resins. They are "rubbery" producing films that are rubber band like. Resins in contrast are not rubbery, but ate hard and because of their higher crosslink density form powders when struck by a hammer.

We have also found that reaction of methyl undecylenate to make the intermediate esters of the present invention provides a finished product that is free of acid value, as opposed to using the fatty acid. Acid value present in the vinyl intermediates causes problems with hydrosilylation.

Crosslinkers

We have surprisingly and unexpectedly found that by using an organic crosslinker of varying lengths the solubility and film forming properties of the resin can be altered allowing for the preparation of customized films.

Crosslinker 1

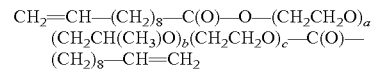

This crosslinker is made by the reaction of polyoxyalkylene glycol and undecylenic acid methyl ester to form an alpha-omega di vinyl crosslinker.

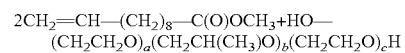

The reaction is carried out at temperatures of between 150° C. and 220° C. Esterification catalysts can be added as required.

Since the vinyl groups react in this class of compounds R' is

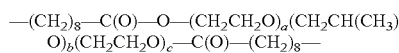

wherein:

a is an integer ranking from 0 to 20;

b is an integer ranking from 0 to 20;

c is an integer ranking from 0 to 20.

Crosslinker 2

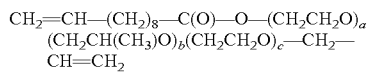

This crosslinker is made by the reaction of allyl alcohol alkoxylate and undecylenic acid methyl ester to form an alpha-omega di vinyl crosslinker

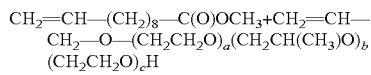

The reaction is carried out at temperatures of between 150° C. and 220° C. Esterification catalysts can be added as required.

Since the vinyl groups react in this class of compounds R' is

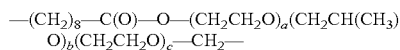

wherein;

a is an integer ranking from 0 to 20;

b is an integer ranking from 0 to 20;

c is an integer ranking from 0 to 20.

Crosslinker 3

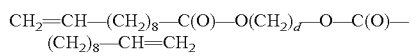

This crosslinker is made by the reaction of a diol and methyl undecylenate to form an alpha-omega di vinyl crosslinker

The reaction is carried out at temperatures of between 150° C. and 220° C. Esterification catalysts can be added as required.

Since the vinyl groups react in this class of compounds R' is

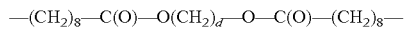

wherein;

d is an integer ranking from 2 to 12.

Crosslinker 4

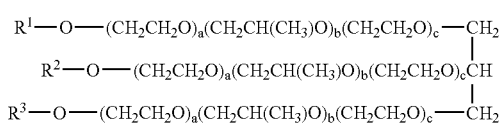

This crosslinker is made by the reaction of a glycerin and its alkoxylates with 2 moles of methyl undecylenate and one mole of a fatty acid to form an alpha-omega di vinyl crosslinker.

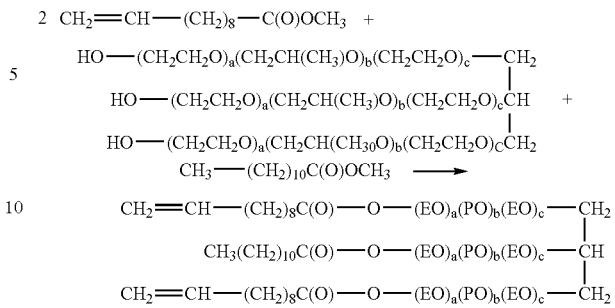

The reaction is carried out at temperatures of between 150° C. and 220° C. Esterification catalysts can be added as required. The preferred catalyst is tin oxylate at 0.1% by weight.

Since the vinyl groups react in this class of compounds R' is

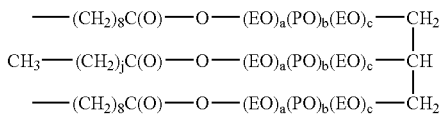

wherein:

j is an integer ranging from 6 to 30.

The present invention relates to a series of compounds made by the hydrosilylation reaction of a silanic hydrogen containing silicone conforming to the following structure:

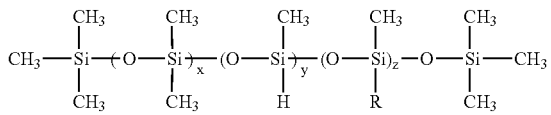

wherein;

x is an integer ranging from 0 to 2000;

y is an integer ranging from 2 to 200;

z is an integer ranging from 0 to 200;

R is selected from the group consisting of H, —$(CH_2)_e$—$CH_3$;

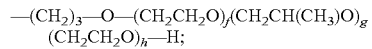

e is an integer ranging from 6 to 35;

f is an integer ranging from 0 to 20;

g is an integer ranging from 0 to 20;

h is an integer ranging from 0 to 20;

and an alpha-omega divinyl compound conforming to the following structure;

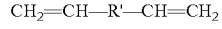

wherein;

R' is selected from the group consisting of:

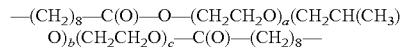 (a)

wherein:
a is an integer ranking from 0 to 20;
b is an integer ranking from 0 to 20;
c is an integer ranking from 0 to 20;

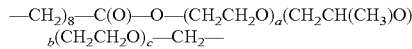
(b)

wherein;
a is an integer ranking from 0 to 20;
b is an integer ranking from 0 to 20;
c is an integer ranking from 0 to 20;

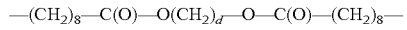
(c)

wherein;
d is an integer ranking from 2 to 12;

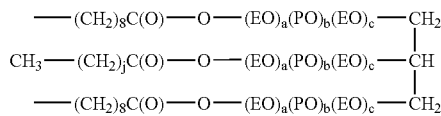

wherein:
j is an integer ranging from 6 to 30, in the presence of a suitable hydrosilylation catalyst;

in a suitable volatile solvent selected from the group consisting of cyclomethicone, hexamethyldisiloxane and isoparaffin.

Another aspect of the present invention relates to a series of compounds made by the hydrosilylation reaction of a silanic hydrogen containing silicone conforming to the following structure:

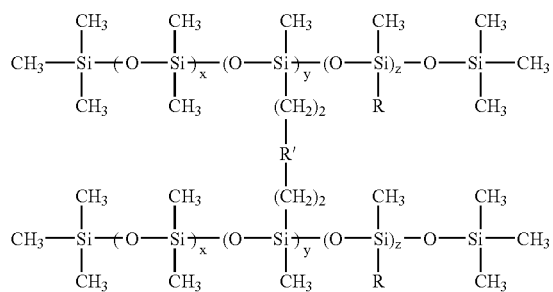

wherein:
x is an integer ranging from 0 to 2000;
y is an integer ranging from 2 to 200;
z is an integer ranging from 0 to 200;
R is selected from the group consisting of H, —(CH$_2$)$_e$—CH$_3$;

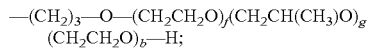

e is an integer ranging from 6 to 35;
f is an integer ranging from 0 to 20;
g is an integer ranging from 0 to 20;
h is an integer ranging from 0 to 20;

R' is selected from the group consisting of:

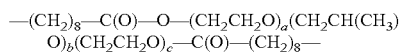
(a)

wherein:
a is an integer ranking from 0 to 20;
b is an integer ranking from 0 to 20;
c is an integer ranking from 0 to 20;

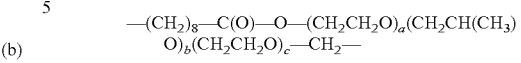
(b)

wherein;
a is an integer ranking from 0 to 20;
b is an integer ranking from 0 to 20;
c is an integer ranking from 0 to 20;

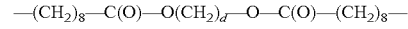
(c)

wherein;
d is an integer ranking from 2 to 12;

and

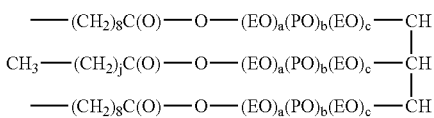

wherein:
j is an integer ranging from 6 to 30.

PREFERRED EMBODIMENTS

In a preferred embodiment x is an integer ranging from 1 to 200.
In a preferred embodiment y is an integer ranging from 2 to 20.
In a preferred embodiment z is an integer ranging from 1 to 20.
In a preferred embodiment R is H.
In a preferred embodiment R is —(CH$_2$)$_e$—CH$_3$.
In a preferred embodiment R is —(CH$_2$)$_3$—O—(CH$_2$CH$_2$O)$_f$(CH$_2$CH(CH$_3$)O)$_g$(CH$_2$CH$_2$O)$_h$—H.

In a preferred embodiment e is an integer ranging from 10 to 17.
In a preferred embodiment f is an integer ranging from 1 to 10.
In a preferred embodiment g is an integer ranging from 1 to 10.
In a preferred embodiment h is an integer ranging from 1 to 10.
In a preferred embodiment R' is

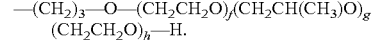

In a preferred embodiment R' is

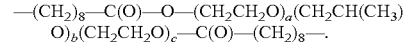

In a preferred embodiment R' is

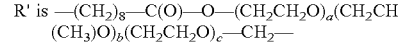

In a preferred embodiment R' is

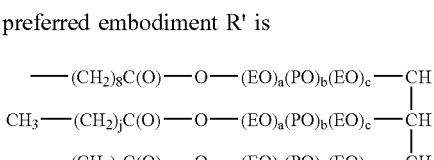

EXAMPLES

Raw Materials

Example 1

Methyl Undecylenate

Methyl undecylenate is an item of commerce available from a variety of sources. It conforms to the following structure:

$$CH_2\!=\!CH\!-\!(CH_2)_8\!-\!C(O)OCH_3$$

Examples 2-9 Polyoxyalkylene Glycols

Polyoxyalkylene glycols (also called PEGs and PPGs) are items of commerce made by a variety of suppliers, including Siltech Corporation in Toronto Canada. They conform to the following structure:

$$HO\!-\!(CH_2CH_2O)_a\!-\!(CH_2CH(CH_3)O)_b\!-\!(CH_2CH_2O)_cH$$

wherein;
a is an integer ranking from 0 to 20;
b is an integer ranking from 0 to 20;
c is an integer ranking from 0 to 20;

| Example | a | b | c |
|---|---|---|---|
| 2 | 0 | 1 | 0 |
| 3 | 18 | 6 | 5 |
| 4 | 5 | 5 | 5 |
| 5 | 0 | 20 | 0 |
| 6 | 2 | 5 | 10 |
| 7 | 0 | 0 | 10 |
| 8 | 10 | 5 | 10 |
| 9 | 20 | 20 | 20 |

Examples 10-17 Allyl Alcohol Alkoxylatyes

Allyl alcohol alkoxylates are items of commerce made by a variety of suppliers, including Siltech Corporation in Toronto Canada. They conform to the following structure:

$$HO\!-\!(CH_2CH_2O)_a(CH_2CH(CH_3)O)_b(CH_2CH_2O)_c\!-\!CH_2CH\!=\!CH_2$$

wherein;
a is an integer ranking from 0 to 20;
b is an integer ranking from 0 to 20;
c is an integer ranking from 0 to 20;

| Example | a | b | c |
|---|---|---|---|
| 10 | 0 | 1 | 0 |
| 11 | 18 | 6 | 5 |
| 12 | 5 | 5 | 5 |
| 13 | 0 | 20 | 0 |
| 14 | 2 | 5 | 10 |
| 15 | 0 | 0 | 10 |
| 16 | 10 | 5 | 10 |
| 17 | 20 | 20 | 20 |

Examples 18-34 Fatty Acids

Fatty acids useful as raw materials in the preparation of the compounds of the present invention are commercially available from a variety of sources including Procter and Gamble of Cincinnati Ohio. The structures are well known to those skilled in the art. It is:

$$R\!-\!C(O)\!-\!OH$$

Saturated

| Example | R Formula | Common Name | Molecular Weight |
|---|---|---|---|
| 18 | $C_7H_5$ | caprylic | 144 |
| 19 | $C_9H_{19}$ | capric | 172 |
| 20 | $C_{11}H_{23}$ | lauric | 200 |
| 21 | $C_{13}H_{27}$ | myristic | 228 |
| 22 | $C_{14}H_{29}$ | pentadecanoic | 242 |
| 23 | $C_{15}H_{31}$ | palmitic | 256 |
| 24 | $C_{17}H_{35}$ | stearic | 284 |
| 25 | $C_{19}H_{39}$ | arachidinic | 312 |
| 26 | $C_{21}H_{43}$ | behenic | 340 |
| 27 | $C_{26}H_{53}$ | cetrotic | |
| 28 | $C_{33}H_{67}$ | | |

Unsaturated

| Example | R Formula | Common Name | Molecular Weight |
|---|---|---|---|
| 29 | $C_{17}H_{33}$ | oleic | 282 |
| 30 | $C_{17}H_{31}$ | linoleic | 280 |
| 31 | $C_{17}H_{29}$ | linolenic | 278 |
| 32 | $C_{15}H_{29}$ | palmitoleic | 254 |
| 33 | $C_{13}H_{25}$ | myristicoleic | 226 |
| 34 | $C_{21}H_{41}$ | erucic | 333 |

Examples 35-39 Diols

Diols suitable as reactants in the present invention are available from several suppliers. One supplier is JarChem located in Newark, N.J. They conform the following structure:

$$HO\!-\!(CH_2)_d OH$$

wherein;
d is an integer ranking from 2 to 12;

| Example | d |
|---|---|
| 35 | 2 |
| 36 | 8 |
| 37 | 10 |
| 38 | 12 |
| 39 | 18 |

Examples 40-47 Glycerin Alkoxylates

Glycerin alkoxylates are items of commerce made by a variety of suppliers, including Siltech Corporation in Toronto Canada. They conform to the following structure:

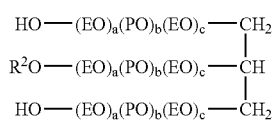

wherein;
a is an integer ranking from 0 to 20;
b is an integer ranking from 0 to 20;
c is an integer ranking from 0 to 20.

| Example | a | b | c | R² |
|---------|----|----|----|----|
| 40 | 0 | 1 | 0 | Caprylic (Example 18) |
| 41 | 18 | 6 | 5 | Lauric (Example 20) |
| 42 | 5 | 5 | 5 | Cetrotic (Example 27) |
| 43 | 0 | 20 | 0 | Oleic (Example 29) |
| 44 | 2 | 5 | 10 | Erucic (Example 34) |
| 45 | 0 | 0 | 10 | Behenic (Example 26) |
| 46 | 10 | 5 | 10 | Stearic (Example 24) |
| 47 | 20 | 20 | 20 | Pentadecanoic (Example 22) |

Silanic Hydrogen Silicone Compounds

Examples 48-58

Silanic Hydrogen compounds are items of commerce made by a variety of suppliers, including Siltech Corporation in Toronto Canada. They conform to the following structure:

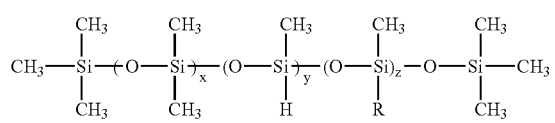

wherein;
x is an integer ranging from 0 to 2000;
y is an integer ranging from 2 to 200;
z is an integer ranging from 0 to 200;
R is selected from the group consisting of H, —$(CH_2)_e$—$CH_3$;

—$(CH_2)_3$—O—$(CH_2CH_2O)_f(CH_2CH(CH_3)O)_g$$(CH_2CH_2O)_h$—H;

e is an integer ranging from 6 to 35;
f is an integer ranging from 0 to 20;
g is an integer ranging from 0 to 20;
h is an integer ranging from 0 to 20.

Crosslinker Preparation

General Procedure

The crosslinkers are made by the transesterification reaction of methyl undecylenate and a variety of hydroxy containing compounds. The reason the methyl ester is used, rather than the acid, is the fact that there is no residual acid value after the reaction is compete. This gives faster and cleaner hydrosilylation reactions.

To the specified number of grams of undecylenate is added the specified number of grams of the specified hydroxy containing compound. A catalyst is recommended, although the reaction can be run without one. Preferred catalyst is stannous oxylate. The reaction mixture is heated to 150-200° C. Methanol will distill off as reaction proceeds. The amount of methanol distilled off is measured and used to monitor the reaction. The reaction is also monitored by gas chromatography and saponification value.

Crosslinker 1

Examples 59-66 $CH_2$=CH—$(CH_2)_8$—C(O)—O—$(EO)_a(PO)_b(EO)_c$—C(O)—$(CH_2)_8$—CH=$CH_2$ This product is made by the reaction of methyl undecylenate (example 1) and PEG or PPG materials (examples 2-9), using the conditions described as General Procedure.

| | PEG/PPG | | | |
|---|---|---|---|---|
| Example | Example | Grams | Example | Grams |
| 59 | 2 | 38.5 | 1 | 210.0 |
| 60 | 3 | 305.0 | 1 | 210.0 |
| 61 | 4 | 269.0 | 1 | 210.0 |
| 62 | 5 | 599.0 | 1 | 210.0 |
| 63 | 6 | 377.5 | 1 | 210.0 |
| 64 | 7 | 229.0 | 1 | 210.0 |
| 65 | 8 | 381.5 | 1 | 210.0 |
| 66 | 9 | 1049.0 | 1 | 210.0 |

| Example | x | y | z | R | f | g | h | e |
|---------|-----|-----|-----|---|---|---|---|---|
| 48 | 0 | 2 | 0 | None | None | None | None | None |
| 49 | 10 | 5 | 20 | —$(CH_2)_e CH_3$ | None | None | None | 6 |
| 50 | 15 | 20 | 15 | —$(CH_2)_3 O(EO)_f(PO)_g(EO)_h H$ | 0 | 0 | 0 | None |
| 51 | 25 | 50 | 9 | —H | None | None | None | None |
| 52 | 50 | 25 | 50 | —$(CH_2)_3 O(EO)_f(PO)_g(EO)_h H$ | 10 | 5 | 10 | None |
| 53 | 75 | 15 | 0 | None | None | None | None | None |
| 54 | 100 | 28 | 5 | —H | None | None | None | None |
| 55 | 5 | 5 | 15 | —$(CH_2)_3 O(EO)_f(PO)_g(EO)_h H$ | 20 | 20 | 20 | None |
| 56 | 10 | 150 | 10 | —$(CH_2)_e CH_3$ | None | None | None | 35 |
| 57 | 6 | 100 | 200 | —$(CH_2)_3 O(EO)_f(PO)_g(EO)_h H$ | 0 | 10 | 0 | None |
| 58 | 2000 | 200 | 0 | None | None | None | None | None |

Crosslinker 2

Examples 67-74 $CH_2=CH-(CH_2)_8-C(O)-O-(EO)_a(PO)_b(EO)_c-CH_2-CH=CH_2$

This product is made by the reaction of methyl undecylenate (example 1) and allyl alcohol alkoxylates (examples 10-17), using the conditions described as General Procedure.

| Allyl Alkoxylates | | | | |
|---|---|---|---|---|
| Example | Example | Grams | Example | Grams |
| 67 | 10 | 116.0 | 1 | 210.0 |
| 68 | 11 | 649.0 | 1 | 210.0 |
| 69 | 12 | 577.0 | 1 | 210.0 |
| 70 | 13 | 1237.0 | 1 | 210.0 |
| 71 | 14 | 794.0 | 1 | 210.0 |
| 72 | 15 | 497.0 | 1 | 210.0 |
| 73 | 16 | 802.0 | 1 | 210.0 |
| 74 | 17 | 2137.0 | 1 | 210.0 |

Crosslinker 3

Examples 75-79 $CH_2=CH-(CH_2)_8-C(O)-O-(CH_2)_d-O-C(O)-(CH_2)_8-CH=CH_2$

This product is made by the reaction of methyl undecylenate (example 1) and a diol (examples 35-39), using the conditions described as General Procedure.

| Diol | | | | |
|---|---|---|---|---|
| Example | Example | Grams | Example | Grams |
| 75 | 35 | 31.0 | 1 | 210.0 |
| 76 | 36 | 73.0 | 1 | 210.0 |
| 77 | 37 | 87.0 | 1 | 210.0 |
| 78 | 38 | 101.0 | 1 | 210.0 |
| 79 | 39 | 143.0 | 1 | 210.0 |

Crosslinker 4

Examples 80-87

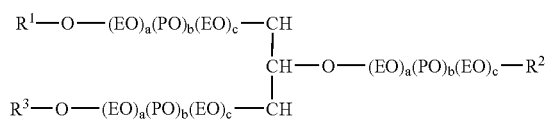

$R^1$, $R^2$ and $R^3$ are independently selected from the group consisting of; H;

$CH_2=CH-(CH_2)_8-C(O)-$ and $CH_3(CH_2)_d-C(O)-$ d is an integer ranging from 6 to 30;

This product is made by the reaction of methyl undecylenate (example 1) and a glycerin ethoxylate (examples 40-47), using the conditions described as General Procedure.

| Glycerin Alkoxylate | | | | |
|---|---|---|---|---|
| Example | Example | Grams | Example | Grams |
| 80 | 40 | 132.5 | 1 | 210.0 |
| 81 | 41 | 324.0 | 1 | 210.0 |
| 82 | 42 | 393.0 | 1 | 210.0 |
| 83 | 43 | 439.0 | 1 | 210.0 |
| 84 | 44 | 498.0 | 1 | 210.0 |
| 85 | 45 | 438.0 | 1 | 210.0 |
| 86 | 46 | 477.5 | 1 | 210.0 |
| 87 | 47 | 869.0 | 1 | 210.0 |

Hydrosilylation Compounds of the Present Invention

Hydrosilylation Solvents

Examples 88-91

The hydrosilylation reactions are advantageously run in a volatile solvent, which can later be distilled off is desired. It is also a practice to sell the products in solvent.

| Example | Description |
|---|---|
| 88 | isopropanol |
| 89 | isododecane |
| 90 | cyclomethicone |
| 91 | isodecane |

Hydrosilylation

Hydrosilylation is a process that reacts terminal vinyl compounds with silanic hydrogen to obtain a Si—C bond. References to this reaction, incorporated herein by reference, include:

U.S. Pat. Nos. 3,715,334 and 3,775,452 to Karstedt, shows the use of Pt(O) complex with vinylsilicon siloxane ligands as an active hydrosilylation catalyst.

Additional platinum complexes, such as complexes with platinum halides are shown by, U.S. Pat. No. 3,159,601 Ashby and, U.S. Pat. No. 3,220,972, to Lamoreaux.

Another hydrosilylation catalyst is shown by Fish, U.S. Pat. No. 3,576,027. Fish prepares a platinum(IV) catalyst by reacting crystalline platinum(IV) chloroplatinic acid and organic silane or siloxane to form a stable reactive platinum hydrosilylation catalyst.

General Procedure

To the specified number of grams of the specified solvent is added the specified number of grams of the specified silanic hydrogen compound. The mass is mixed well. To that mixture is added the specified number of grams of the specified vinyl compound. The reaction mass is mixed well until homogeneous. To that mixture is added 0.1% Karstedt catalyst, which is commercially available from Geleste. The agitation is stopped and the reaction begins. The reaction mass will thicken over 4 hours. Once the maximum viscosity is reached the reaction is considered complete. The solvent may be distilled off or the product may be sold as prepared without additional purification.

Class 1 Polymers Examples 92-99

| Ex- | Vinyl compound | | Silanic Hydrogen | | Solvent | |
|---|---|---|---|---|---|---|
| ample | Example | Grams | Example | Grams | Example | Grams |
| 92 | 59 | 23.6 | 48 | 15.4 | 88 | 781.8 |
| 93 | 60 | 50.3 | 49 | 91.4 | 89 | 1417.0 |
| 94 | 61 | 46.7 | 50 | 19.2 | 90 | 439.3 |
| 95 | 62 | 79.7 | 51 | 12.6 | 91 | 184.7 |
| 96 | 63 | 57.5 | 52 | 578.6 | 88 | 6361.0 |
| 97 | 64 | 42.7 | 53 | 763.6 | 89 | 8063.0 |
| 98 | 65 | 57.9 | 54 | 745.1 | 90 | 8030.1 |
| 99 | 66 | 124.7 | 55 | 65.7 | 91 | 1904.0 |

The nature of the crosslinking group has a profound effect upon functionality of the resin. In this case the group is:

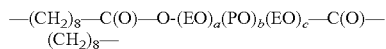

—(CH$_2$)$_8$—C(O)—O-(EO)$_a$(PO)$_b$(EO)$_c$—C(O)—(CH$_2$)$_8$—

The key to understanding the functionality of the resin of the present invention is an appreciation that silicone, oil and water are three mutually immiscible groups. This lack of solubility is the cause of the syneresis (or separation) seen in pigmented products that contain oil, silicone and water. If the molecule has all three groups properly connected the molecule will orientate itself into the lowest free energy. In this configuration the polar, non-polar and silicone portions of the resin and of the formulation will all associate in a matrix. The parts of this linking group that connect to the silicone group are oil soluble. The length of that group is fairly long and symmetrical. The internal group is water loving (polar). Resins with this configuration allows for the incorporation of both oil loving (non-polar non-silicone) and water loving (polar) into a matrix. This produces an emollient property to the skin in a film forming matrix. Both water and oil can be easily accommodated in the formulation. The presence of the ester group helps biodegradability.

Class 2 Polymers

Examples 100-107

| Ex- | Vinyl compound | | Silanic Hydrogen | | Solvent | |
|---|---|---|---|---|---|---|
| ample | Example | Grams | Example | Grams | Example | Grams |
| 100 | 67 | 31.4 | 58 | 1534.1 | 88 | 15655.0 |
| 101 | 68 | 84.7 | 57 | 95.9 | 89 | 1606.0 |
| 102 | 69 | 77.5 | 56 | 13.6 | 90 | 912.0 |
| 103 | 70 | 143.5 | 55 | 65.7 | 91 | 2092.0 |
| 104 | 71 | 99.2 | 54 | 745.1 | 88 | 8443.0 |
| 105 | 72 | 69.5 | 53 | 763.6 | 89 | 8331.0 |
| 106 | 73 | 99.9 | 52 | 578.6 | 90 | 6786.0 |
| 107 | 74 | 233.5 | 51 | 12.6 | 91 | 2461.0 |

The nature of the crosslinking group has a profound effect upon functionality of the resin. In this case the group is:

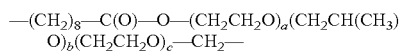

—(CH$_2$)$_8$—C(O)—O—(CH$_2$CH$_2$O)$_a$(CH$_2$CH(CH$_3$)O)$_b$(CH$_2$CH$_2$O)$_c$—CH$_2$—

In this configuration, the only one side of the crosslinker is fatty. The other is a short CH$_2$ group. The resin will orientate itself differently in the presence of silicone, polar and non-polar groups. This type of resin has increased polar affinity. That is an ability to solubilize polar materials. This produces an moisturizing product in a film forming matrix. The presence of the ester group improves biodegradability.

Class 3 Polymers

Examples 108-112

| Ex- | Vinyl compound | | Silanic Hydrogen | | Solvent | |
|---|---|---|---|---|---|---|
| ample | Example | Grams | Example | Grams | Example | Grams |
| 108 | 75 | 22.9 | 50 | 192.0 | 88 | 421.0 |
| 109 | 76 | 27.1 | 49 | 914.0 | 89 | 1185.0 |
| 110 | 77 | 28.5 | 48 | 154.0 | 90 | 878.0 |
| 111 | 78 | 29.9 | 48 | 154.0 | 91 | 906.0 |
| 112 | 79 | 34.1 | 49 | 914.0 | 88 | 2510.0 |

The nature of the crosslinking group has a profound effect upon functionality of the resin. In this case the group is:

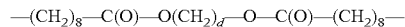

—(CH$_2$)$_8$—C(O)—O(CH$_2$)$_d$—O—C(O)—(CH$_2$)$_8$—

In this configuration, type of group present in the crosslinker is fatty. However the fatty group is long and has polar ester linkages. The resin will orientate itself differently in the presence of silicone, polar and non-polar groups. This type of resin has increased oil affinity. That is an ability to solubilize oil minimizes syneresis and solubilizes the oily esters present in lipsticks. The presence of the ester group also improves biodegradation.

Class 4 Polymers Examples 113-120

| Ex- | Vinyl compound | | Silanic Hydrogen | | Solvent | |
|---|---|---|---|---|---|---|
| ample | Example | Grams | Example | Grams | Example | Grams |
| 113 | 80 | 33.0 | 50 | 19.2 | 88 | 1044.0 |
| 114 | 81 | 54.0 | 51 | 12.6 | 89 | 1333.2 |
| 115 | 82 | 59.1 | 52 | 578.6 | 90 | 12754.0 |
| 116 | 83 | 63.7 | 53 | 763.6 | 91 | 16546.0 |
| 117 | 84 | 69.6 | 54 | 745.1 | 88 | 16294.0 |
| 118 | 85 | 63.6 | 55 | 65.7 | 89 | 2586.0 |
| 119 | 86 | 675.5 | 56 | 136.8 | 90 | 1624.0 |
| 120 | 87 | 1067.0 | 57 | 959.0 | 90 | 4152.0 |

The nature of the crosslinking group has a profound effect upon functionality of the resin. In this case the group is:

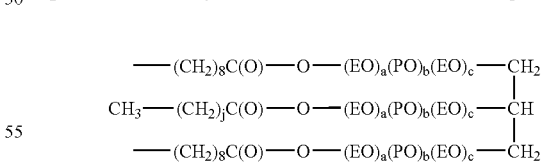

In this configuration, type of group present in the crosslinker is quite large and branched. It contains an appreciable polar group, including a free ester group. The resin will orientate itself differently in the presence of silicone, polar and non-polar groups. This type of resin has a low viscosity due to the branching and has a great deal of elastic properties. That is an ability to solubilize oil minimizes syneresis and solubilize the oily esters present in lipsticks. The presence of the ester group also improves biodegradation.

As is clear the ability to change the linking group within a resin results in a variety of changes in the ability to make personal care products that have desirable properties. This relates to the ability to keep oil soluble materials, water soluble materials and silicone soluble materials in the same formulation, providing a cosmetically acceptable product. The products of the present invention allow for greater formulation latitude and also allow for the introduction of new products hereto for not attainable.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

I claim:

1. A silicone polymer made by the hydrosilylation reaction of a silanic hydrogen containing silicone conforming to the following structure:

$$CH_3-Si(CH_3)_2-(O-Si(CH_3)_2)_x-(O-Si(CH_3))_y-(O-Si(R)_2)_z-O-Si(CH_3)_2-CH_3$$
(with H on the y silicon and R on the z silicons)

wherein;

x is an integer ranging from 0 to 2000;
y is an integer ranging from 2 to 200;
z is an integer ranging from 0 to 200;
R is selected from the group consisting of $-(CH_2)_e-CH_3$;

$-(CH_2)_3-O-(CH_2CH_2O)_f(CH_2CH(CH_3)O)_g(CH_2CH_2O)_h-H$;

e is an integer ranging from 6 to 35;
f is an integer ranging from 0 to 20;
g is an integer ranging from 0 to 20;
h is an integer ranging from 0 to 20;

and an alpha-omega divinyl compound conforming to the following structure;

$CH_2=CH-R'-CH=CH_2$ wherein;
R' is selected from the group consisting of:

$-(CH_2)_8-C(O)-(CH_2CH_2O)_a(CH_2CH(CH_3)O)_b(CH_2CH_2O)_c-C(O)-(CH_2)_8-$ (a)

wherein:
a is an integer ranking from 0 to 20;
b is an integer ranking from 0 to 20;
c is an integer ranking from 0 to 20;

$-(CH_2)_8-C(O)-O(CH_2CH_2O)_a(CH_2CH(CH_3)O)_b(CH_2CH_2O)_c-CH_2-$ (b)

wherein;
a is an integer ranking from 0 to 20;
b is an integer ranking from 0 to 20;
c is an integer ranking from 0 to 20;

$-(CH_2)_8-C(O)-O(CH_2)_d-O-C(O)-(CH_2)_8-$ (c)

wherein;
d is an integer ranking from 2 to 12;

$$\begin{array}{l}-(CH_2)_8C(O)-O-(EO)_a(PO)_b(EO)_c-CH\\CH_3-(CH_2)_jC(O)-O-(EO)_a(PO)_b(EO)_c-CH\\-(CH_2)_8C(O)-O-(EO)_a(PO)_b(EO)_c-CH\end{array}$$ (d)

wherein:
j is an integer ranging from 6 to 30;
in the presence of a suitable hydrosilylation catalyst;
in a suitable volatile solvent selected from the group consisting of cyclomethicone, hexamethyldisiloxane and isoparaffin.

2. A silicone polymer of claim 1 wherein x is an integer ranging from 1 to 200.

3. A silicone polymer of claim 1 wherein y is an integer ranging from 2 to 20.

4. A silicone polymer of claim 1 wherein z is an integer ranging from 1 to 20.

5. A silicone polymer of claim 1 wherein R is $-(CH_2)_e-CH_3$.

6. A silicone polymer of claim 1 herein R is $-(CH_2)_3-OCH_2CH_2O)_f(CH_2CH(CH_3)O)_g(CH_2CH_2O)_b-H$.

7. A silicone polymer of claim 1 wherein e is an integer ranging from 10 to 17.

8. A silicone polymer of claim 1 wherein f is an integer ranging from 1 to 10.

9. A silicone polymer of claim 1 wherein g is an integer ranging from 1 to 10.

10. A silicone polymer of claim 1 wherein h is an integer ranging from 1 to 10.

11. A silicone polymer of claim 1 wherein R' is $-(CH_2)_8-C(O)-O-(CH_2CH_2O)_a(CH_2CH(CH_3)O)_b(CH_2CH_2O)_c-C(O)-(CH_2)_8-$.

12. A silicone polymer of claim 1 wherein R' is $-(CH_2)_8-C(O)-O(CH_2CH_2O)_a(CH_2CH(CH_3)O)_b(CH_2CH_2O)_c-CH_2-$.

13. A silicone polymer of claim 1 wherein R' is $-(CH_2)_8-C(O)O(CH_2)_d-O-C(O)-(CH_2)_8-$.

14. A silicone polymer of claim 1 wherein R' is $$\begin{array}{l}-(CH_2)_8C(O)-O-(EO)_a(PO)_b(EO)_c-CH\\CH_3-(CH_2)_jC(O)-O-(EO)_a(PO)_b(EO)_c-CH\\-(CH_2)_8C(O)-O-(EO)_a(PO)_b(EO)_c-CH.\end{array}$$

15. A silicone polymer conforming to the following structure:

$$CH_3-Si(CH_3)(CH_3)-(O-Si(CH_3)(CH_3))_x-(O-Si(CH_3)((CH_2)_2-R'))_y-(O-Si(CH_3)(R))_z-O-Si(CH_3)(CH_3)-CH_3$$

$$CH_3-Si(CH_3)(CH_3)-(O-Si(CH_3)(CH_3))_x-(O-Si(CH_3)((CH_2)_2-))_y-(O-Si(CH_3)(R))_z-O-Si(CH_3)(CH_3)-CH_3$$

wherein:
- x is an integer ranging from 0 to 2000;
- y is an integer ranging from 2 to 200;
- z is an integer ranging from 0 to 200;
- R is selected from the group consisting of —$(CH_2)_e$—$CH_3$;

—$(CH_2)_3$—O—$(CH_2CH_2O)_f(CH_2CH(CH_3)O)_g$$(CH_2CH_2O)_h$—H;

- e is an integer ranging from 6 to 35;
- f is an integer ranging from 0 to 20;
- g is an integer ranging from 0 to 20;
- h is an integer ranging from 0 to 20;

R' is selected from the group consisting of:

—$(CH_2)_8$—C(O)—O$(CH_2CH_2O)_a(CH_2CH(CH_3)O)_b$$(CH_2CH_2O)_c$—(O)—$(CH_2)_8$—  (a)

wherein:
- a is an integer ranking from 0 to 20;
- b is an integer ranking from 0 to 20;
- c is an integer ranking from 0 to 20;

—$(CH_2)_8$—C(O)O—$(CH_2CH_2O)_a(CH_2CH(CH_3)O)_b$$(CH_2CH_2O)_c$—$CH_2$—  (b)

wherein;
- a is an integer ranking from 0 to 20;
- b is an integer ranking from 0 to 20;
- c is an integer ranking from 0 to 20;

—$(CH_2)_8$—C(O)—O$(CH_2)_d$—O—C(O)—$(CH_2)_8$—  (c)

wherein;
- d is an integer ranking from 2 to 12;

and $$\begin{array}{l} —(CH_2)_8C(O)—O—(EO)_a(PO)_b(EO)_c—CH \\ CH_3—(CH_2)_jC(O)—O—(EO)_a(PO)_b(EO)_c—CH \\ —(CH_2)_8C(O)—O—(EO)_a(PO)_b(EO)_c—CH \end{array}$$  (d)

wherein:
j is an integer ranging from 6 to 30.

16. A silicone polymer of claim 15 wherein x is an integer ranging from 1 to 200.

17. A silicone polymer of claim 15 wherein y is an integer ranging from 2 to 20.

18. A silicone polymer of claim 15 wherein z is an integer ranging from 1 to 20.

19. A silicone polymer of claim 15 wherein R is —$(CH_2)_e$—$CH_3$.

20. A silicone polymer of claim 15 wherein R is

—$(CH_2)_3$—O—$(CH_2CH_2O)_f(CH_2CH(CH_3)O)_g$$(CH_2CH_2O)_h$—.

21. A silicone polymer of claim 15 wherein e is an integer ranging from 10 to 17.

22. A silicone polymer of claim 15 wherein f is an integer ranging from 1 to 10.

23. A silicone polymer of claim 15 wherein g is an integer ranging from 1 to 10.

24. A silicone polymer of claim 15 wherein h is an integer ranging from 1 to 10.

25. A silicone polymer of claim 15 wherein R' is

—$(CH_2)_8$—C(O)O—$(CH_2CH_2O)_a(CH_2CH(CH_3)O)_b$$(CH_2CH_2O)_c$—C(O)—$(CH_2)_8$—.

26. A silicone polymer of claim 15 wherein R' is

R' is —$(CH_2)_8$—C(O)—O—$(CH_2CH_2O)_a(CH_2CH(CH_3)O)_b(CH_2CH_2O)_c$—$CH_2$—.

27. A silicone polymer of claim 15 wherein R' is

—$(CH_2)_8$—C(O)—O$(CH_2)_d$—O—C(O)—$(CH_2)_8$—.

28. A silicone polymer of claim 15 wherein R' is $$\begin{array}{l} —(CH_2)_8C(O)—O—(EO)_a(PO)_b(EO)_c—CH \\ CH_3—(CH_2)_jC(O)—O—(EO)_a(PO)_b(EO)_c—CH \\ —(CH_2)_8C(O)—O—(EO)_a(PO)_b(EO)_c—CH. \end{array}$$

* * * * *

UNITED STATES PATENT AND TRADEMARK OFFICE
CERTIFICATE OF CORRECTION

PATENT NO. : 7,361,721 B1  Page 1 of 1
APPLICATION NO. : 11/257964
DATED : April 22, 2008
INVENTOR(S) : O'Lenick, Jr.

It is certified that error appears in the above-identified patent and that said Letters Patent is hereby corrected as shown below:

In Claim 1

Delete

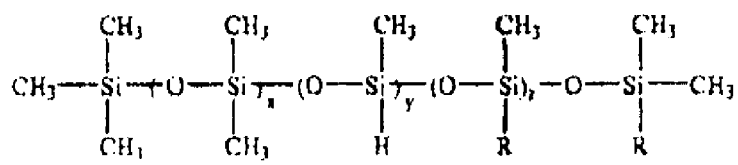

And insert therefore

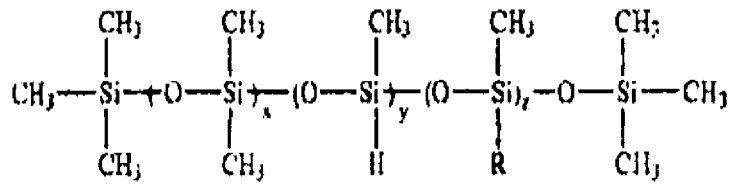

Signed and Sealed this

Twelfth Day of August, 2008

JON W. DUDAS
*Director of the United States Patent and Trademark Office*